United States Patent
Luhta et al.

(10) Patent No.: US 8,532,251 B2
(45) Date of Patent: Sep. 10, 2013

(54) MULTI-DETECTOR ARRAY IMAGING SYSTEM

(75) Inventors: Randall P. Luhta, Highland Heights, OH (US); Marc A. Chappo, Elyria, OH (US); Brian E. Harwood, Rocky River, OH (US); Rodney A. Mattson, Mentor, OH (US); Chris John Vrettos, Willoughby, OH (US)

(73) Assignee: Koninklijke Philips N.V., Eindhoven (NL)

( * ) Notice: Subject to any disclaimer, the term of this patent is extended or adjusted under 35 U.S.C. 154(b) by 65 days.

(21) Appl. No.: 13/319,151

(22) PCT Filed: Apr. 15, 2010

(86) PCT No.: PCT/IB2010/051648
§ 371 (c)(1),
(2), (4) Date: Nov. 7, 2011

(87) PCT Pub. No.: WO2010/136911
PCT Pub. Date: Dec. 2, 2010

(65) Prior Publication Data
US 2012/0057670 A1 Mar. 8, 2012

Related U.S. Application Data

(60) Provisional application No. 61/181,707, filed on May 28, 2009.

(51) Int. Cl.
*A61B 6/00* (2006.01)
(52) U.S. Cl.
USPC .......................................................... 378/19

(58) Field of Classification Search
USPC ............................................................ 378/19
See application file for complete search history.

(56) References Cited

U.S. PATENT DOCUMENTS

| | | | |
|---|---|---|---|
| 4,845,731 A | 7/1989 | Vidmar et al. | |
| 4,969,165 A * | 11/1990 | Bernardi et al. | 378/13 |
| 5,400,379 A | 3/1995 | Pfoh et al. | |
| 5,475,726 A * | 12/1995 | Azevedo et al. | 378/4 |
| 6,041,097 A * | 3/2000 | Roos et al. | 378/62 |
| 6,346,706 B1 * | 2/2002 | Rogers et al. | 250/363.04 |
| 7,016,457 B1 * | 3/2006 | Senzig et al. | 378/19 |
| 7,470,914 B2 | 12/2008 | Li et al. | |
| 7,473,901 B2 | 1/2009 | Scholz | |
| 2002/0071517 A1 * | 6/2002 | Hoffman | 378/19 |
| 2003/0002626 A1 | 1/2003 | Hoheisel et al. | |
| 2004/0032927 A1 * | 2/2004 | Hoffman | 378/19 |
| 2005/0147201 A1 * | 7/2005 | Hoffman | 378/15 |

(Continued)

FOREIGN PATENT DOCUMENTS

| | | |
|---|---|---|
| EP | 1266620 A2 | 12/2002 |
| WO | 2007054837 A2 | 5/2007 |

(Continued)

*Primary Examiner* — Alexander H Taningco

(57) ABSTRACT

An imaging system (100) includes a radiation source (108) that emits radiation that traverses an examination region (106) and a detection system (114) that detects radiation that traverses the examination region (106) and generates a signal indicative thereof. The detection system (114) includes a first detector array ($114_1$-$114_N$) and a second detector array ($114_1$-$114_N$). The first and second detector arrays ($114_1$-$114_N$) are separately distinct detector arrays and at least one of the detector arrays ($114_1$-$114_N$) is moveable with respect to the radiation beam. A reconstructor (116) reconstructs the signal and generates volumetric image data indicative thereof.

22 Claims, 9 Drawing Sheets

(56) References Cited

U.S. PATENT DOCUMENTS

| | | | |
|---|---|---|---|
| 2005/0173641 A1* | 8/2005 | Unger et al. | 250/370.09 |
| 2005/0259783 A1* | 11/2005 | Hoffman | 378/19 |
| 2006/0140340 A1 | 6/2006 | Kravis | |
| 2006/0222143 A1* | 10/2006 | Du | 378/11 |
| 2008/0069298 A1 | 3/2008 | Hoffman et al. | |
| 2008/0101535 A1* | 5/2008 | Wu et al. | 378/19 |
| 2009/0016593 A1* | 1/2009 | Ma | 382/132 |
| 2010/0119139 A1* | 5/2010 | Bertram et al. | 382/131 |
| 2010/0215142 A1* | 8/2010 | Dafni et al. | 378/19 |
| 2011/0129059 A1* | 6/2011 | Kobayashi | 378/8 |

FOREIGN PATENT DOCUMENTS

| | | |
|---|---|---|
| WO | 2007092877 A2 | 8/2007 |
| WO | 2008135994 A2 | 11/2008 |
| WO | 2009060344 A2 | 5/2009 |

* cited by examiner

MULTI-DETECTOR ARRAY IMAGING SYSTEM

CROSS REFERENCE TO RELATED APPLICATIONS

This application claims the benefit of U.S. provisional application Ser. No. 61/181,707 filed May 28, 2009, which is incorporated herein by reference.

DESCRIPTION

The following generally relates to an imaging system configured to receive and employ more than one detector array, and is described in connection with computer tomography (CT). However, it is also amenable to other medical and non-medical imaging applications.

A computed tomography (CT) scanner generally includes an x-ray tube and a detector array mounted on a rotating gantry opposite each other across an examination region. The rotating gantry is rotatably supported by a generally stationary gantry and is configured to rotate around the examination region. The detector array includes a one or two-dimensional array of photosensors. With a conventional integrating scanner, the detector array has included an array of scintillator pixels optically coupled to an array of photodiode pixels.

For scanning purposes, the rotating gantry and hence the x-ray tube and detector array rotate around the examination region. The x-ray tube emits radiation that traverses the examination region (and an object or subject disposed therein) and illuminates the detector array. The scintillator pixels detect the radiation and generate light indicative thereof. The photodiode pixels detect the light and generate a signal indicative thereof. A reconstructor processes the signal and generates volumetric image data indicative of the scanned object or subject. The volumetric image data can be processed to generate one or more images of the object or subject.

The detector array in such a scanner has been configured for a predetermined set of conventional scanning modes, and not advanced scanning modes such as spectral CT, photon counting, or high resolution. Unfortunately, adapting the detector array to provide such advanced scanning modes may result in significantly increasing the overall cost of the scanner. In addition, adapting the detector array as such may reduce the performance of the scanner for the non-advanced scanning modes. Examples of reduced performance include reduced coverage, reduced scan speed, reduced maximum tube current, and reduced geometric efficiency.

Aspects of the present application address the above-referenced matters and others.

In one aspect, an imaging system includes a radiation source that emits radiation that traverses an examination region and a detection system that detects radiation that traverses the examination region and generates a signal indicative thereof. The detection system includes a first detector array and a second detector array. The first and second detector arrays are separately distinct detector arrays and at least one of the detector arrays is moveable with respect to the radiation beam. A reconstructor reconstructs the signal and generates volumetric image data indicative thereof.

In another aspect, a method for scanning with an imaging system includes receiving a signal indicative of a scan protocol for scanning an object or subject with the imaging system and identifying a detector array type based on the signal. The identified detector array type corresponds to one of a plurality of detector arrays installed in the imaging system. The method further includes moving a moveable detector array located outside of a path traversed by radiation emitted by a radiation source of the system into the path or maintaining the moveable detector array in the path in response to identifying the moveable detector array as the detector array type.

In another aspect, a method includes installing a stationary detector array in a path traversed by radiation emitted by an imaging system and installing a moveable detector array in the imaging system, wherein the moveable detector array is configured to selectively move into and out of the path for imaging an object or subject.

The invention may take form in various components and arrangements of components, and in various steps and arrangements of steps. The drawings are only for purposes of illustrating the preferred embodiments and are not to be construed as limiting the invention.

Figure 1:
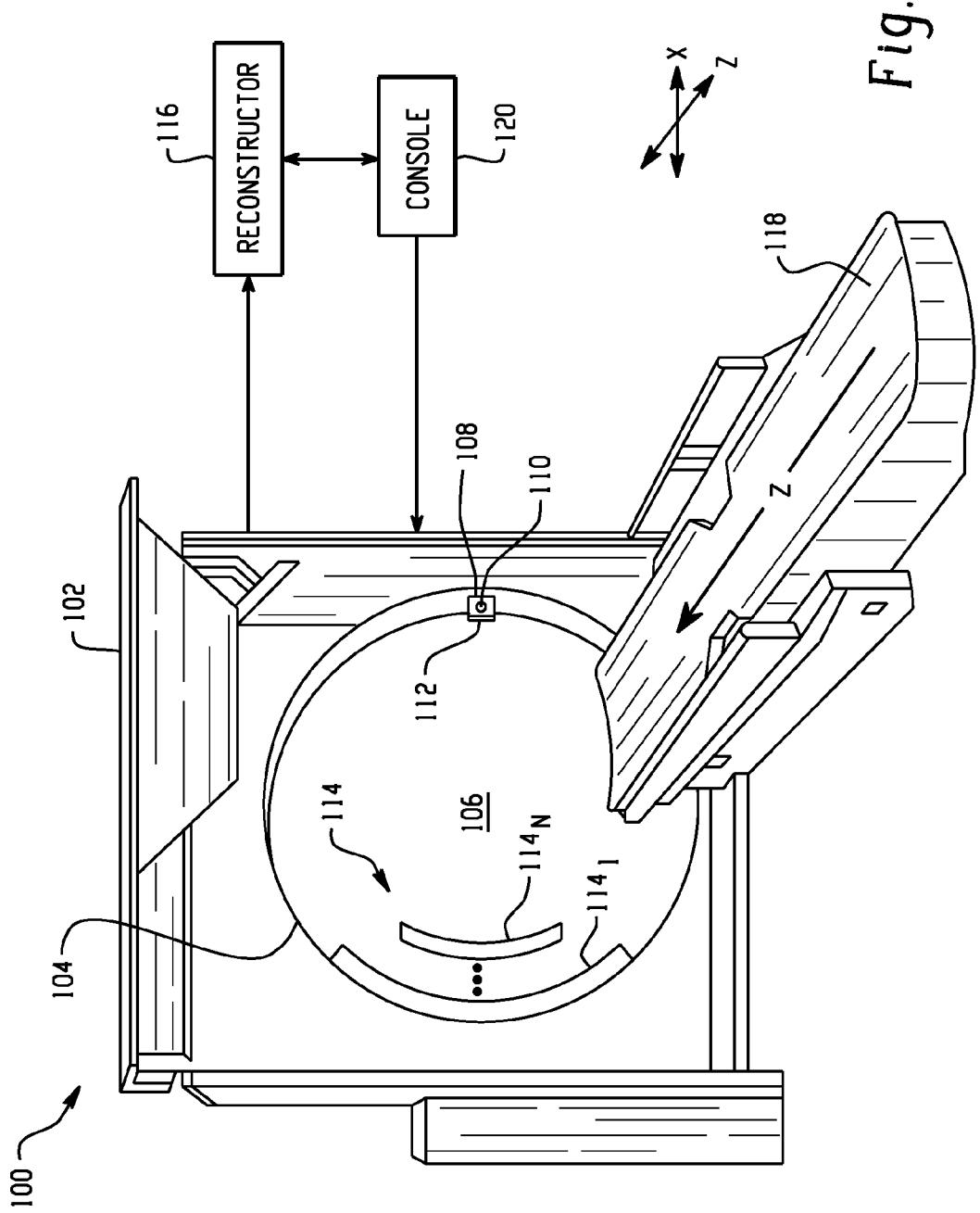
FIG. 1 illustrates an example imaging system.

Initially referring to FIG. 1, an imaging system 100 such as a CT scanner is illustrated. The scanner 100 includes a stationary gantry 102 and a rotating gantry 104, which is rotatably supported by the stationary gantry 102. The rotating gantry 104 rotates around an examination region 106 about a longitudinal or z-axis.

A radiation source 108, such as an x-ray tube, is supported by and rotates with the rotating gantry 104 and emits radiation from a focal spot 110. A source collimator 112 collimates the emitted radiation along the x and z-axes to form a generally cone, fan, wedge, or otherwise shaped radiation beam that traverses the examination region 106.

A radiation detection system 114 subtends an angular arc across from the radiation source 108, opposite the examination region 106, and is supported by the rotating gantry 104. The radiation detection system 114 includes N physically distinct detector arrays $114_1$ to $114_N$, wherein N is an integer equal to or greater than two. Note that the illustrated separation between the detector arrays 114 and the illustrated x-axis extent or coverage of the detector arrays 114 are for explanatory purposes and not limiting.

As described in greater detail below, at least one of the detector arrays 114 is selectively positionable with respect to the radiation beam, and the detector arrays 114 can be employed individually and/or in combination, depending on the system 100 configuration. This allows for configuring the system 100 with at least two different detector arrays, including at least one non-advanced detector array (e.g., a non-high resolution scintillator/photosensor detector array) and at least one advanced detector array (e.g., spectral, photon counting, high resolution, etc.). Alternatively, the system 100 can be configured with at least two advanced detector arrays, having the same or different detectors. In any instance, an advanced detector array may include a single type of advanced detector or multiple types of advanced detectors.

The detector array 114 employed during scanning detects radiation traversing the examination region 106 and generates a signal indicative thereof. A reconstructor 116 reconstructs the signal and generates volumetric image data indicative of the examination region 106, including an object or subject therein. Where more than one of the detector array 114 is employed during scanning, the signal generated by one or more of the detector arrays is reconstructed to generate volumetric image data. Suitable reconstruction algorithms include filtered backprojection, iterative, and the like. The volumetric image data can be used to generate one or more images of the object or subject.

A support 118, such as a couch, supports the object or subject in the examination region 106. The support 118 is movable along the z-axis in coordination with the rotation of the rotating gantry 104 to facilitate helical, axial, or other desired scanning trajectories. A general purpose computing system serves as an operator console 120, which includes human readable output devices such as a display and/or printer and input devices such as a keyboard and/or mouse. Software resident on the console 120 allows the operator to select a scan protocol that employs a particular one of the at least two detector arrays 114 or concurrently more than one of the at least two detector arrays 114.

As briefly noted above, examples of advanced detector arrays include, but are not limited to, spectral, photon counting, and high-resolution detector arrays. A non-limiting example of a spectral detector array includes a double-decker detector with stacked scintillators and photosensors that are located either below the scintillators in a direction of the impinging radiation or adjacent to the stacked scintillators in a direction perpendicular to the impinging radiation. A suitable photon-counting detector array includes direct conversion material such as cadmium telluride (CdTe), cadmium zinc telluride (CZT) or the like. A suitable high-resolution detector array generally has an x and/or z-axis aperture of less than one (1) millimeter (mm) at the detector plane, which is less than the aperture for a non-advanced detector array.

The aforementioned advanced detector arrays (i.e., spectral, photon counting, high resolution, etc.) generally are more costly per unit detection area than non-advanced detector arrays. In such instances, the advanced detector array can be configured with reduced x and/or z-axis coverage to reduce cost. Configuring the system with at least one non-advanced detector array and at least one advanced detector array with reduced coverage, may reduce overall cost of the system 100, relative to a system with an advanced detector array with non-reduced coverage, while maintaining the coverage for the non-advanced detector array.

Advanced detector arrays, such as detector arrays with photon counting detectors, may have lower flux rate capability, relative to a non-advanced detector array. This may reduce the radiation source maximum current limit and/or maximum rotating gantry rotation speed when employing the advanced detector array, relative to employing a non-advanced detector array. Configuring the system with at least one non-advanced detector array and at least one advanced detector array with photon counting detectors, allows for operating the system 100 in photon counting mode, while maintaining the radiation source current limit and rotating gantry rotation speed when scanning with the non-advanced detector array.

Figure 2:
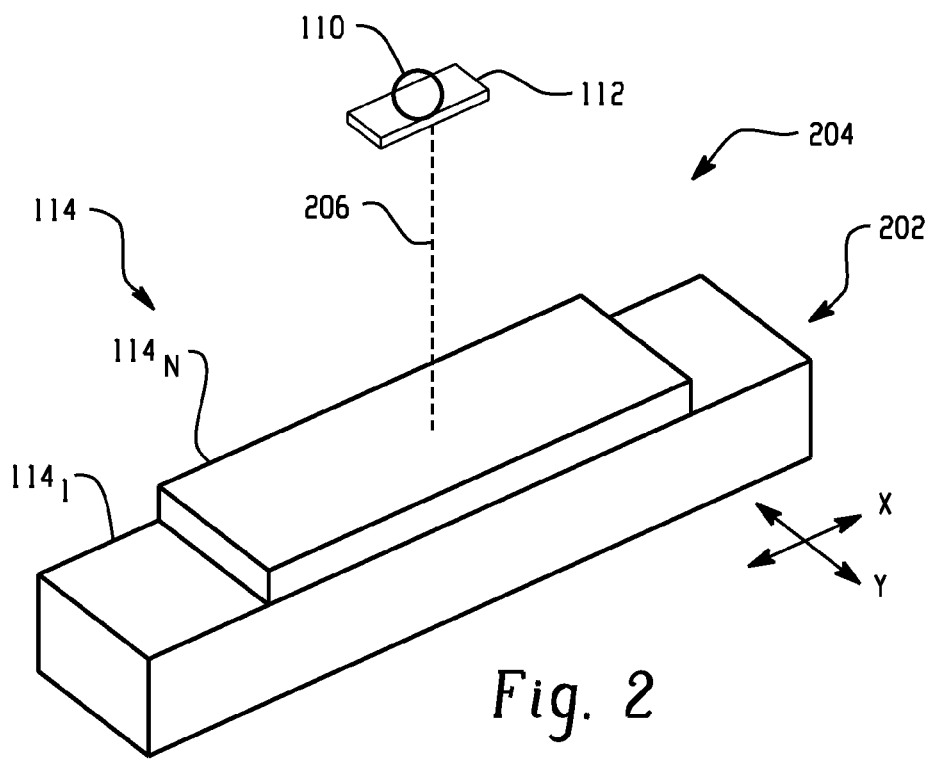
FIGS. 2 and 3 illustrate relative motion between detector arrays.
Figure 3:
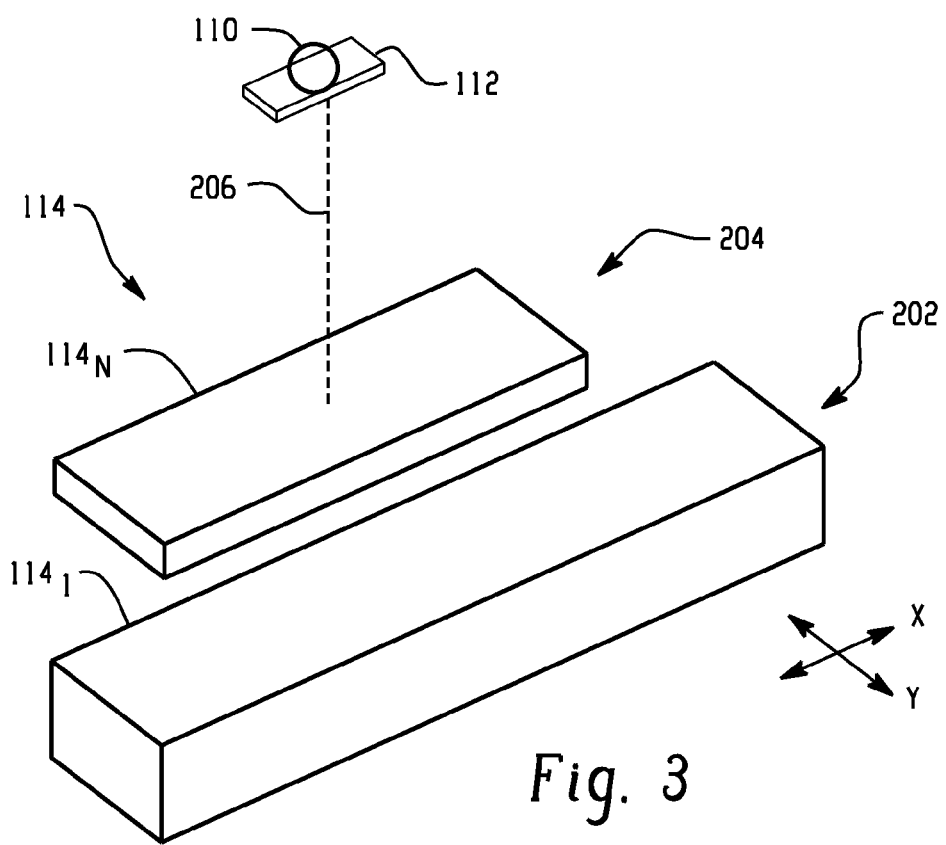

Advanced detector arrays, such as detector arrays with high-resolution detectors, may have a lower geometric efficiency, relative to a non-advanced detector array. Configuring the system with at least one non-advanced detector array and at least one advanced detector array with high resolution detectors, allows for operating the system 100 in high resolution mode, while maintaining the geometric efficiency when scanning with the non-advanced detector array. Moreover, an advanced detector array with high-resolution detectors may improve dose efficiency (and reduce patient dose) relative to a configuration in which comb or other device is used in conjunction with the non-advanced detector array for high-resolution scanning FIGS. 2 and 3 illustrate an example embodiment of the radiation detection system 114 for N=2. In this example, the detector array $114_1$ is stationarily affixed in the detection system 114, and the detector array $114_N$ is movably affixed in the detection system 114. The detector array $114_N$ is configured to move between at least first and second positions 202 and 204.

As shown in FIG. 2, in the first position 202 the detector array $114_N$ is positioned between the detector array $114_1$ and the focal spot 110, over the detector array $114_1$ and in a path 206 traversed by a center ray emitted by the radiation source 108. As shown in FIG. 3, in the second position 204 the detector array $114_N$ is positioned outside of the path 206.

In this embodiment, the x-axis coverage of the detector array $114_N$ is less that the x-axis coverage of the detector array $114_1$. In another embodiment, the x-axis coverage of the detector array $114_N$ and the x-axis coverage of the detectors array $114_1$ are substantially equal. In yet another embodiment, the x-axis coverage of the detector array $114_N$ is greater than the x-axis coverage of the detectors array $114_1$. Likewise, the z-axis coverage of the detector array $114_N$ can be substantially similar (as shown), greater than or less than the z-axis coverage the detector array $114_1$.

In the illustrated embodiment, the detector array $114_1$ includes non-advanced detectors and the detector array $114_N$ includes advanced detectors. In another embodiment, the detector array $114_1$ includes advanced detectors and the detector array $114_N$ includes non-advanced detectors. In yet another embodiment, the detector arrays $114_1$ and $114_N$ both include either non-advanced detectors or advanced detectors.

In the illustrated embodiment, the detector array $114_N$ moves along the z-axis. In another embodiment, the detector array $114_N$ moves along the x-axis. In yet another embodiment, the detector array $114_N$ moves along both the z and x-axes.

Figure 4:
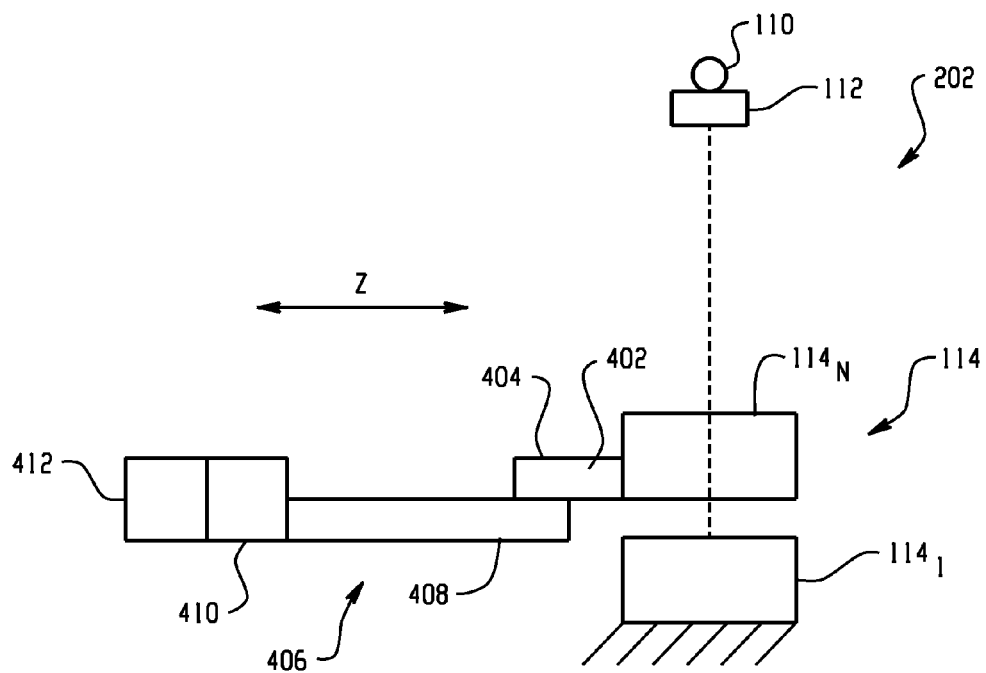
FIGS. 4 and 5 illustrate an approach for moving a detector array.
Figure 5:
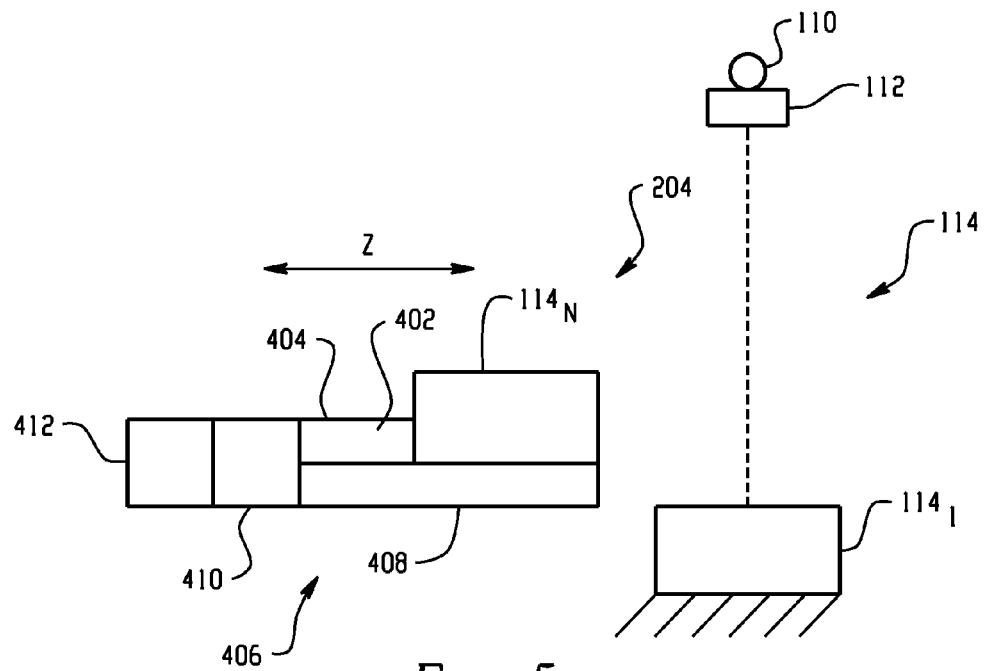

FIGS. 4 and 5 illustrate a non-limiting approach for moving the detector array $114_N$ relative to the radiation beam and between the first and second positions 202 and 204 shown in FIGS. 2 and 3.

In the illustrated embodiment, a platform or moveable support 402 supports the detector array $114_N$. The moveable support 402 can be part of (as shown) or affixed to a first portion 404 of a bearing 406. A second portion 408 of the bearing 406 is stationarily affixed in the detection system 114. Suitable bearings include, but are not limited to, ball bearings, slide bearings, magnetic, and fluid bearings.

A motor 410 drives the moveable support 402 (and hence the detector array $114_N$) between the first position 202 (FIG. 4) and the second position 204 (FIG. 5). A controller 412 controls the motor 410 based on the selected scan protocol or otherwise. An encoder or the like can be used to provide positional information of the moveable support for the controller 412. In another embodiment, the moveable support 402 is moved between positions 202 and 204 via hydraulics or otherwise.

FIGS. 6, 7, 8, and 9 illustrate various scanning modes for the configuration described in connection with FIGS. 2 and 3.

Figure 6:
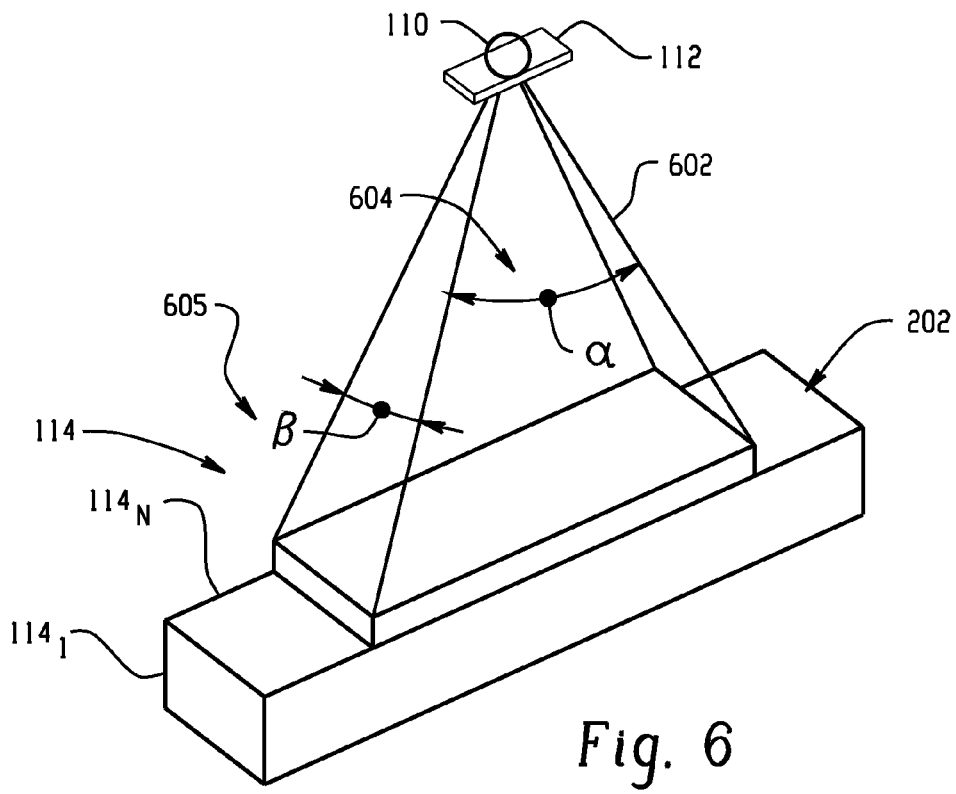
FIGS. 6, 7, 8 and 9 illustrate various scanning configurations.

Initially referring to FIG. 6, in this embodiment the detector array $114_N$ is in the first position 202. In this position, the detector array $114_N$ is positioned over the detector array $114_1$ and in the path of radiation beam 602. The collimator 112 collimates the beam 602 and generates a beam with an x-axis beam angle α 604 and a z-axis beam angle 605 β. In this embodiment, the signal generated by the detector array 114$_N$ is reconstructed to generate volumetric image data.

Figure 7:
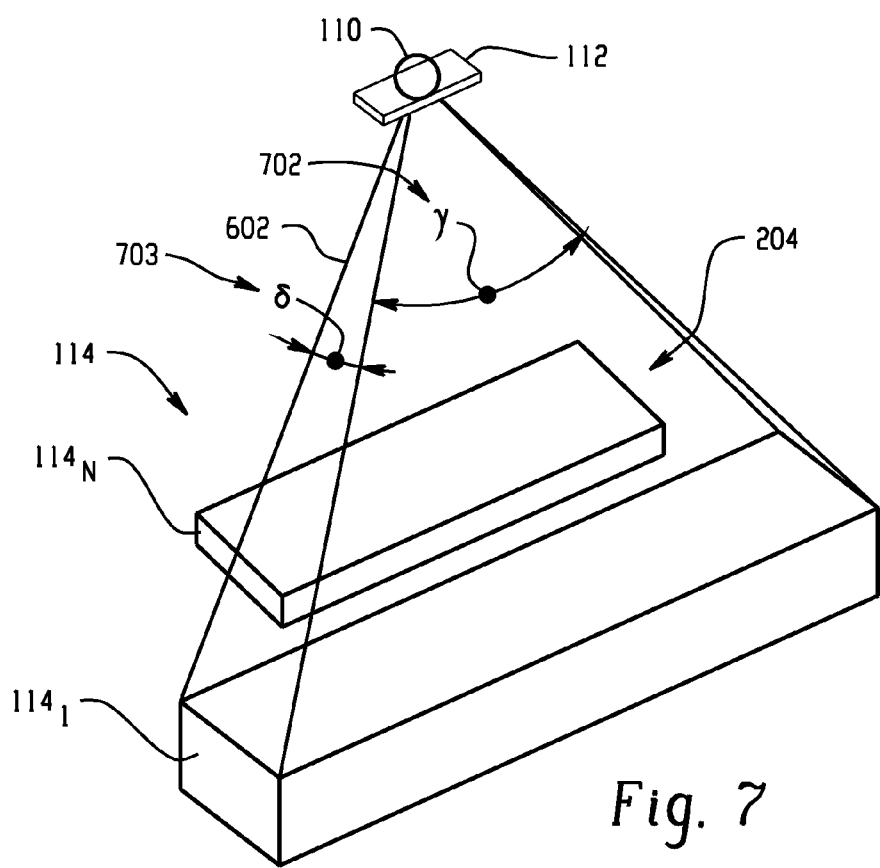

Turning to FIG. 7, in this embodiment the detector array 114$_N$ is in the second position 204. In this position, the detector array 114$_N$ is positioned outside of the path of radiation beam 602. The collimator 112 collimates the beam 602 and generates a beam with an x-axis beam angle γ 702 and a z-axis beam angle δ 703. In this embodiment, the signal generated by the detector array 114$_1$ is reconstructed to generate volumetric image data. In addition, the detector array 114$_1$ can be operated as if the detector array 114$_N$ is omitted from the system 100, including maintaining the same coverage, speed, geometric efficiency and/or flux rate.

Note that in FIGS. 6 and 7, the z-axis coverage of the detector arrays 114$_1$ and 114$_N$ (as defined by angles β and δ) is substantially equal, while the x-axis coverage of the detector array 114$_N$ (defined by angle α) is less than the x-axis coverage of the detector array 114$_1$ (defined by angle γ). In another embodiment, the z-axis coverage of the detectors arrays 114$_1$ and 114$_N$ is substantially equal and the x-axis coverage of the detectors arrays 114$_1$ and 114$_N$ is substantially equal. In yet another embodiment, the x-axis coverage of the detector arrays 114$_1$ and 114$_N$ is substantially equal while the z-axis coverage of the detector array 114$_N$ is less than the z-axis coverage of the detector array 114$_1$. In still another embodiment, the z-axis coverage and the x-axis coverage of the detector array 114$_N$ are respectively less then the z-axis coverage and the x-axis coverage of the detector array 114$_1$.

Figure 8:
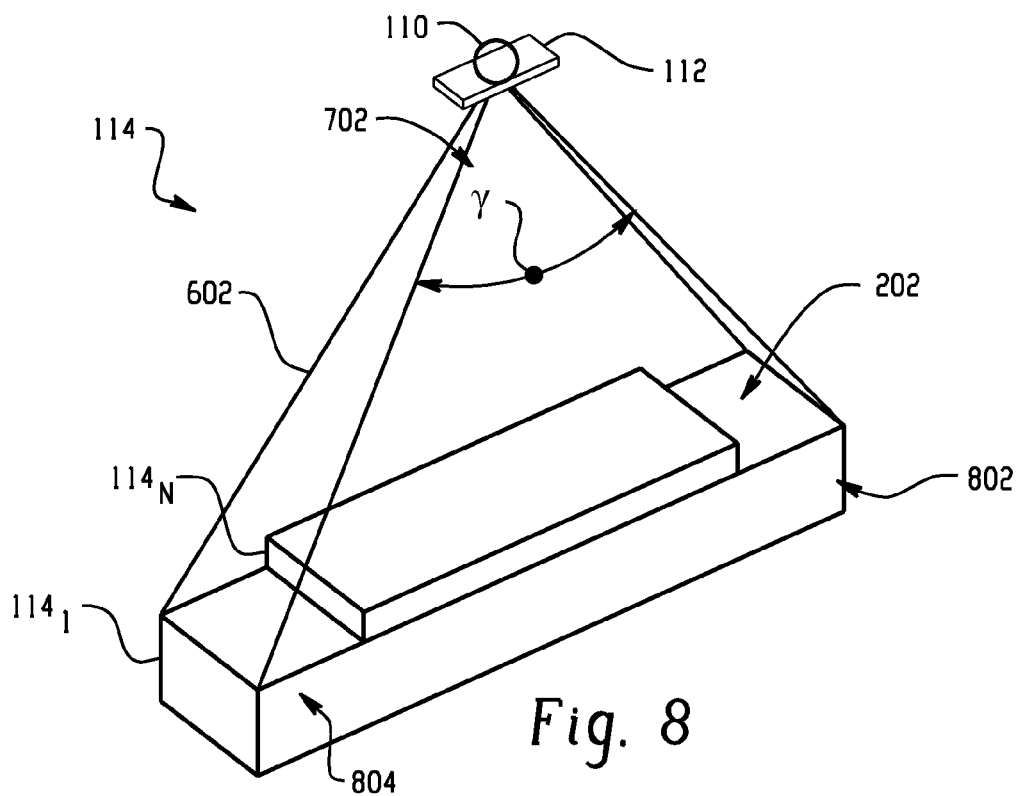

Referring next to FIG. 8, in this embodiment the detector array 114$_N$ is in the first position 202 as described in connection with FIG. 6. However, the collimator 112 collimates the beam 602 to generate a beam with the beam angle γ 702 as described in connection with FIG. 7. The radiation beam 602 illuminates the detector array 114$_N$ and sub-portions 802 and 804 of the detector array 114$_1$ not covered by the detector array 114$_N$.

In this embodiment, the signals generated by one or both of the detector arrays 114$_1$ and 114$_N$ are reconstructed to generate volumetric image data. By way of example, the detector array 114$_N$ may generate incomplete or truncated projections due to reduced x-axis coverage. The signal from the portions 802 and 804 of the detector array 114$_1$ can be combined with the signal from the detector array 114$_N$ to "complete" the incomplete projections.

Figure 9:
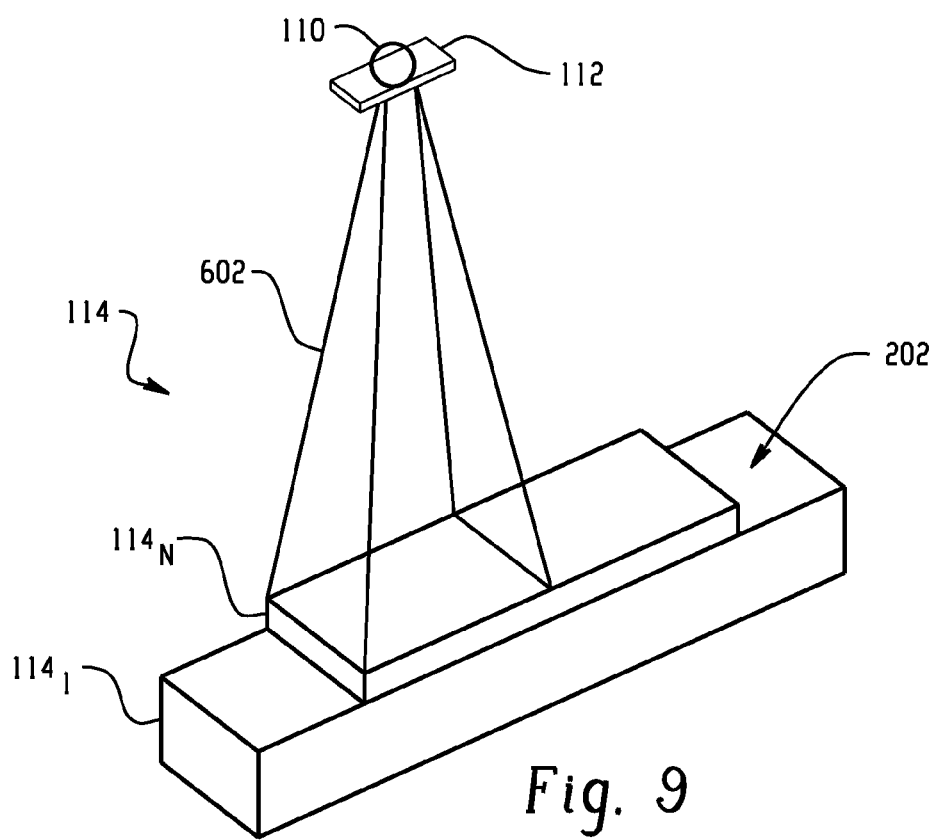

FIG. 9 illustrates an embodiment in which the collimator 112 collimates the beam to generate a beam which asymmetrically illuminates the detector arrays 114$_N$.

Figure 10:
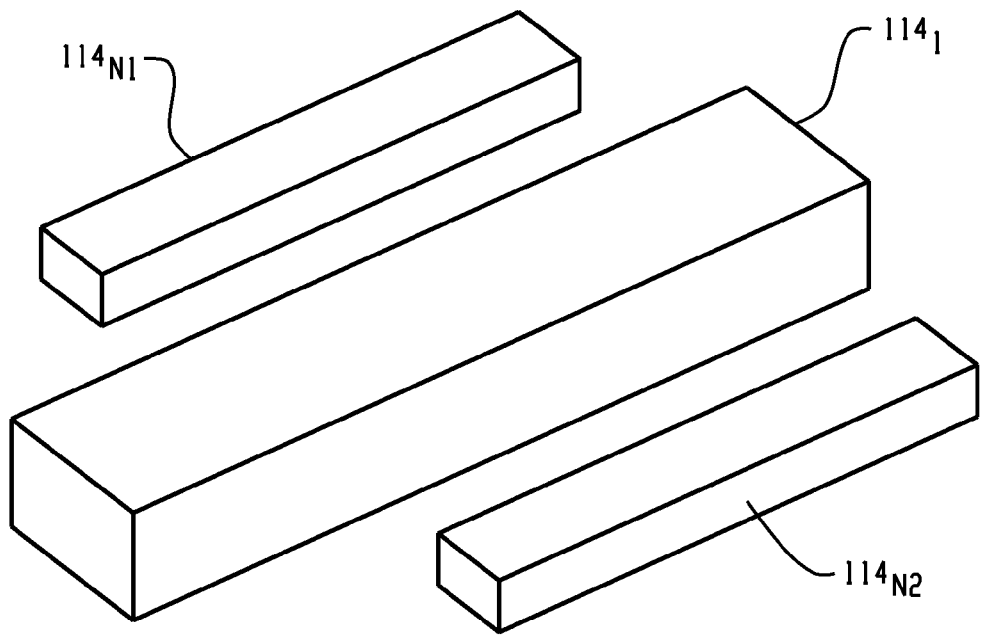
FIGS. 10 and 11 illustrate a moveable split detector array.
Figure 11:
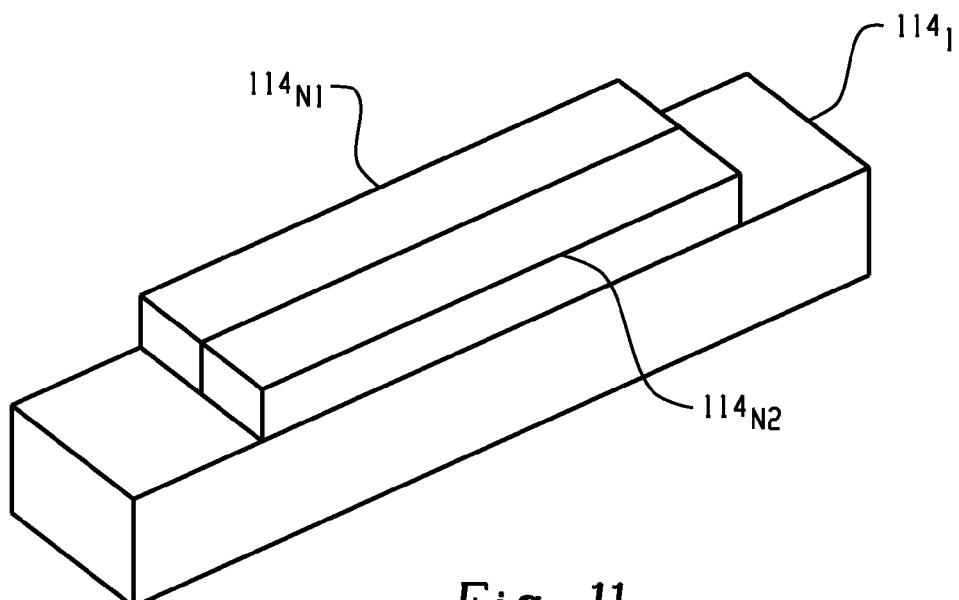

FIGS. 10 and 11 illustrate an embodiment in which the detector array 114$_N$ includes first and second independently moveable portions 114$_{N1}$ and 114$_{N2}$. The moveable portions 114$_{N1}$ and 114$_{N2}$ translate along the z-axis and come together over the detector array 114$_1$ to form the detector array 114$_N$.

Figure 12:
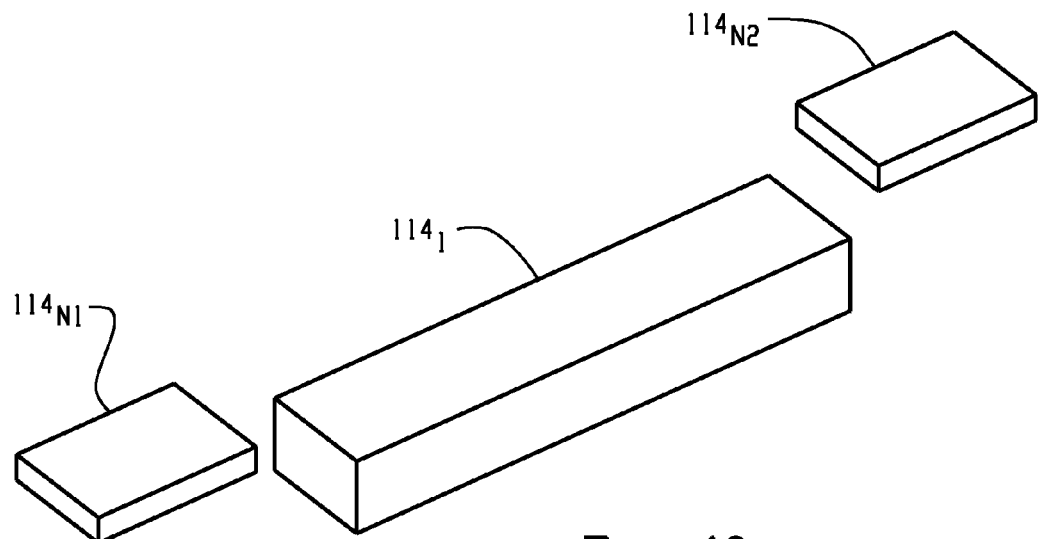
FIGS. 12 and 13 illustrate another moveable split detector array.
Figure 13:
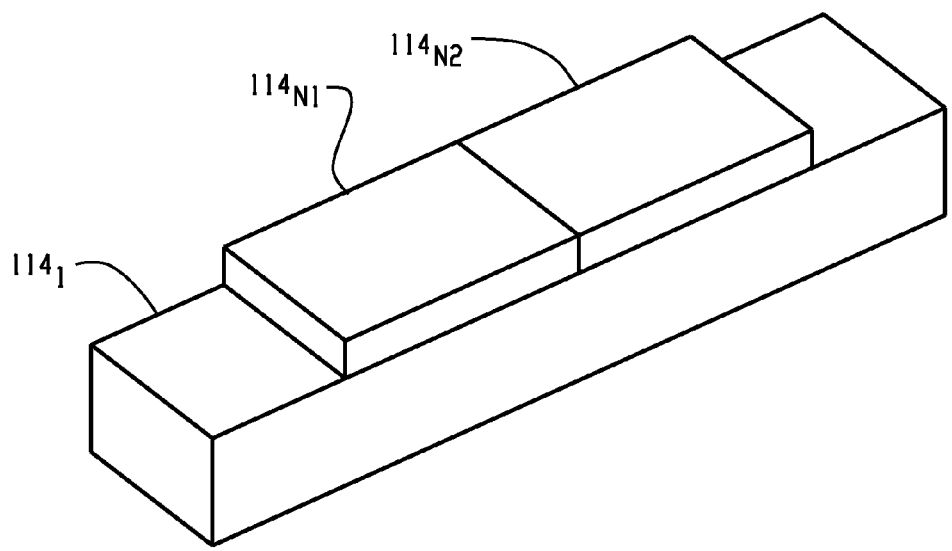

FIGS. 12 and 13 illustrate another embodiment in which the detector array 114$_N$ includes first and second independently moveable portions 114$_{N1}$ and 114$_{N2}$. In this embodiment, the moveable portions 114$_{N1}$ and 114$_{N2}$ translate along the x-axis and come together over the detector array 114$_1$ to form the detector array 114$_N$.

Figure 14:
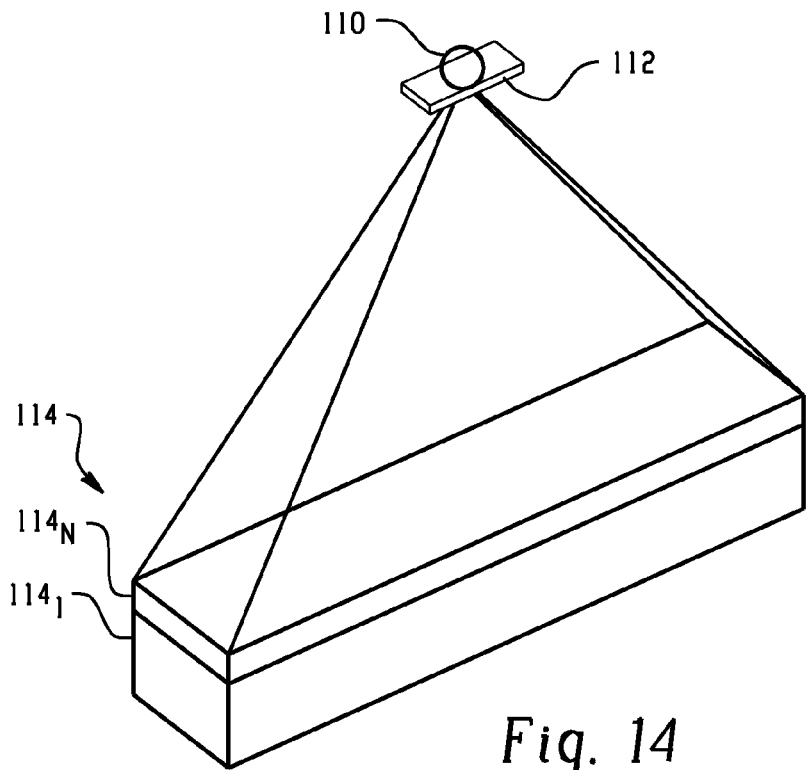
FIG. 14 illustrates an embodiment with equal size detector arrays.

FIG. 14 illustrates an embodiment in which the detector arrays 114$_1$ and 114$_N$ have the substantially the same coverage.

Figure 15:
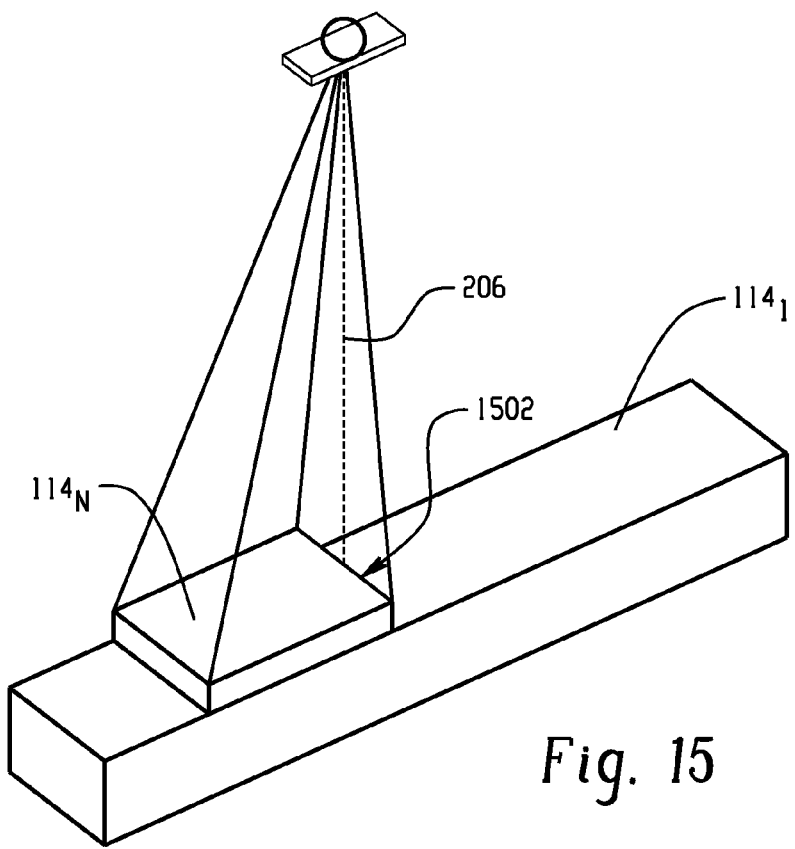
FIG. 15 illustrates a selectively positionable detector array.

FIG. 15 illustrates an embodiment in which the detector array 114$_N$ is selectively positionable in the beam. In the illustrated embodiment, the detector array 114$_N$ can translate along both the x and z-axis and is asymmetrically positioned, or positioned off center with respect to the detector array 114$_1$. In the illustrated embodiment, an edge 1502 of the detector array 114$_N$ is at about the radiation centerline 206. In another embodiment, the edge 1502 extends over the radiation centerline 206. Using such an asymmetrical beam allows for reducing the area of the detector, as shown, which may reduce detector cost.

Figure 16:
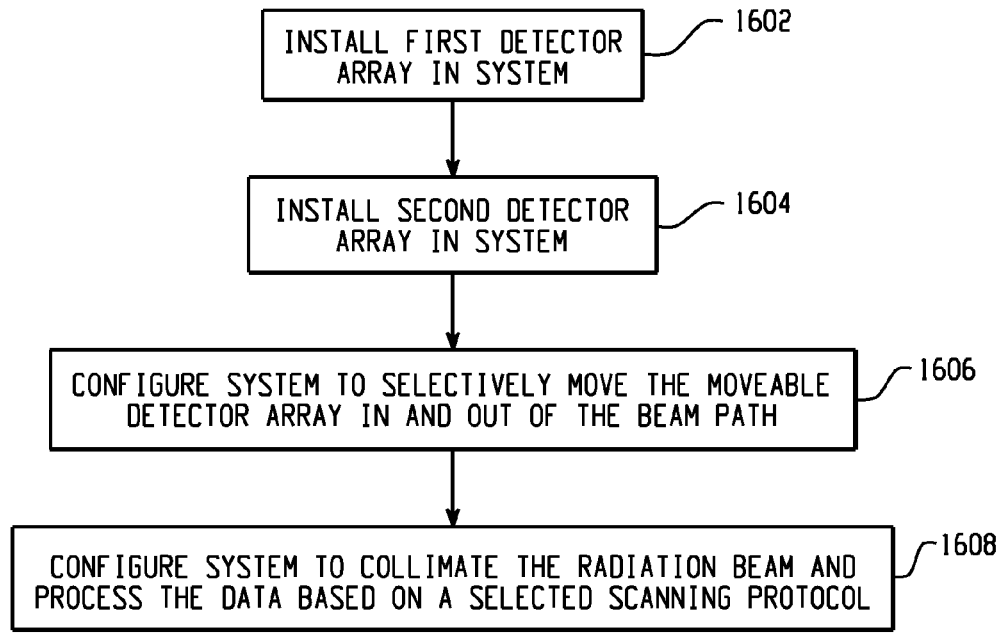
FIGS. 16 and 17 illustrate example methods.

In the embodiments described above, the detector array 114$_1$ is stationary and the detector array 114$_N$ is moveable. In another embodiment, the detector array 114$_1$ is moveable and the detector array 114$_N$ is stationary. In yet another embodiment, both of the detector arrays 114$_1$ and 114$_N$ are moveable FIG. 16 illustrates an example method. At 1602, a first detector array is installed in the imaging system. The first detector array is installed across the radiation source, opposite the examination region 106. At 1604, a second detector array is installed in the imaging system. Likewise, the second detector array is installed across the radiation source, opposite the examination region 106. One of the first or second detector arrays 114$_1$, 114$_N$ is stationarily affixed in the system 100 and the other detector array 114$_1$, 114$_N$ is moveably affixed in the system 100. At 1606, the system 100 is configured to selectively move the moveable detector in the path that emitted radiation traverses or out of the path based on a selected scanning protocol. At 1608, the system 100 is configured to collimate the emitted radiation and process data from one or both of the detector arrays based on a selected scanning protocol.

Figure 17:
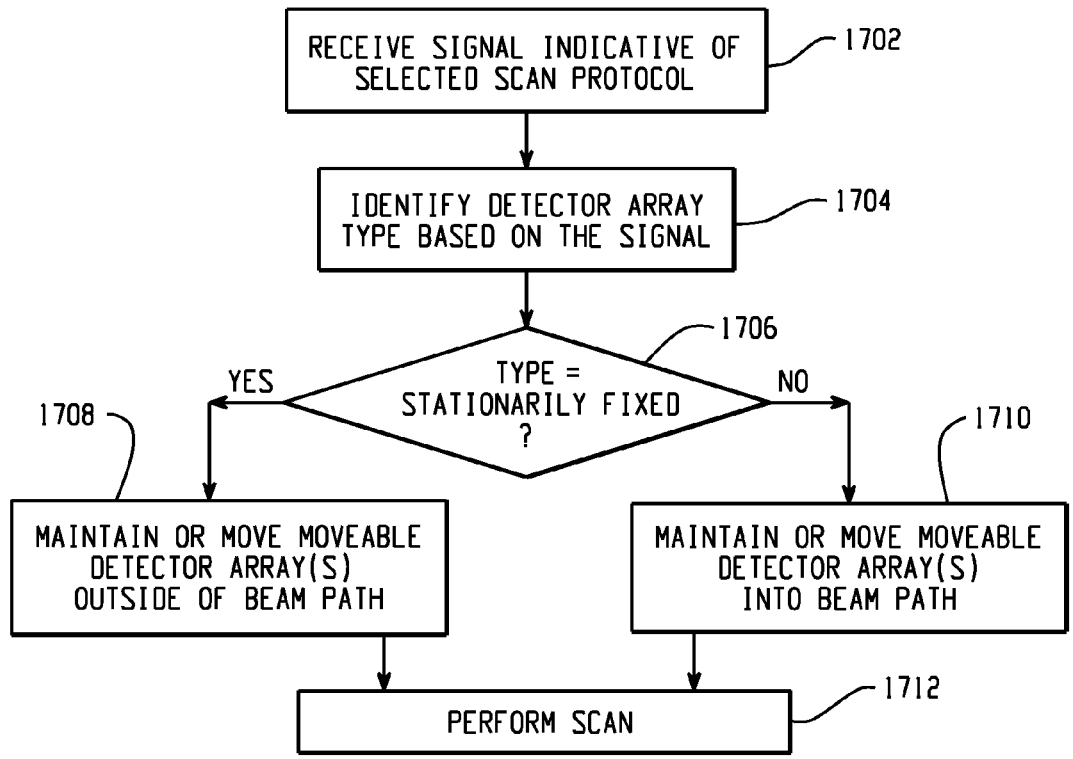

FIG. 17 illustrates an example method. At 1702, a signal indicative of a selected scan protocol is received. At 1704, a detector array type is identified based on the scan protocol. The detector array type is selected from a plurality of types of detector arrays installed in the imaging system 100. At 1706, if the identified detector array corresponds to a stationarily affixed detector array, then at 1708 any moveably affixed detector array is maintained or moved outside of the path that emitted radiation traverses. Alternatively, at 1710, if the identified detector array corresponds to a moveably affixed detector array, then a suitable moveably affixed detector array is maintained in or moved into the path that emitted radiation traverses. At 1712, the scan is performed.

The above can be implemented by way of computer readable instructions, which when executed by a computer processor(s), cause the processor(s) to carry out the described acts. In such a case, the instructions are stored in a computer readable storage medium associated with or otherwise accessible to the relevant computer.

It is to be appreciated that the imaging system 100 can be configured as described herein and include only a single detector array. In such an instance, one or more additional detector arrays can be subsequently installed in the system. This allows a customer to purchase the scanner 100 with a particular type of detector array 114 and later add another type of detector array 114. In another instance, the different type of detector arrays could alternatively be swapped with the single detector array. In either instance, the single detector array can be a non-advanced or an advanced detector array. Additionally or alternatively, the additional detector array can be a non-advanced or an advanced detector array.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
    a radiation source that emits radiation that traverses an examination region;
    a detection system that detects radiation that traverses the examination region and generates a signal indicative thereof, the detection system, including:
        a first detector array; and
        a second detector array, wherein the first and second detector arrays are separately distinct detector arrays and at least one of the detector arrays is mechanically moveable with respect to the detection system and into a path the radiation beam from a location outside of the radiation beam; and
    a reconstructor that reconstructs the signal and generates volumetric image data indicative thereof.

2. The imaging system of claim 1, wherein at least one of the detector arrays includes an advanced detector array.

3. The imaging system of claim 2, wherein the advanced detector array is one of a spectral detector array, a photon counting detector array or a high resolution integrating detector array.

4. The imaging system of claim 2, wherein at least one of the detector arrays includes a non-high resolution integrating detector array.

5. The imaging system of claim 1, wherein at least one of an x-axis or z-axis coverage of one of the at least one of the detector arrays is greater than a corresponding one of an x-axis or z-axis coverage of the other of the at least one of the detector arrays.

6. The imaging system of claim 1, wherein an x-axis and z-axis coverage of one of the at least one of the detector arrays is substantially the same as an x-axis and z-axis coverage of the other of the at least one of the detector arrays.

7. The imaging system of claim 1, wherein the signal includes a signal generated by only one of the at least one of the detector arrays.

8. The imaging system of claim 1, wherein the signal includes a first signal generated by the first detector array and a second signal generated by the second detector array.

9. The imaging system of claim 8, wherein the moveable detector array includes at least two different types of advanced detectors.

10. The imaging system of claim 1, wherein the moveable detector arrays is moveable between a first position in which the detector array is in a path traversed by emitted radiation and a second position in which the detector array is outside of the path.

11. The imaging system of claim 1, wherein the moveable detector array is moveable along a z-axis direction.

12. The imaging system of claim 1, wherein the moveable detector array is moveable along an x-axis direction.

13. The imaging system of claim 1, wherein the moveable detector array is moveable along both an x-axis and a z-axis direction.

14. The imaging system of claim 1, wherein the moveable detector array is configured to be asymmetrically located in the radiation beam.

15. A method for scanning with an imaging system, comprising:
    receiving a signal indicative of a scan protocol for scanning an object or subject with the imaging system;
    identifying a detector array type based on the signal, wherein the identified detector array type corresponds to one of a plurality of detector arrays installed in the imaging system;
    moving a moveable detector array located outside of a path traversed by radiation emitted by a radiation source of the system into the path or maintaining the moveable detector array in the path in response to identifying the moveable detector array as the detector array type.

16. The method of claim 15, further comprising:
    moving the moveable detector array outside of the path or maintaining the moveable detector array outside of the path in response to identifying a different detector array as the detector array type.

17. The method of claim 15, wherein at least one of the detector arrays includes one or more of a spectral detector array, a photon counting detector array or a high-resolution integrating detector array, and another one of the detector arrays includes a non-high resolution integrating detector array.

18. The method of claim 15, further comprising: employing a single one of the detector arrays for the scan.

19. The method of claim 15, further comprising: concurrently employing two or more of the detector arrays for the scan.

20. The method of claim 19, further comprising: utilizing projection data from one of the two or more detector arrays to correct for truncated projection data of another of the two or more detector arrays.

21. The method of claim 15, further comprising: selectively collimating a radiation beam of the imaging system based on a geometry of the identified detector array type.

22. A method, comprising:
    installing a stationary detector array in a path traversed by radiation emitted by an imaging system; and
    installing a moveable detector array in the imaging system, wherein the moveable detector array is configured to selectively move, relative to the imaging system, into and out of the path for imaging an object or subject.

* * * * *